United States Patent [19]

Holtkamp

[11] Plant 4,498

[45] Jan. 29, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No:: 966,226

[22] Filed: Dec. 4, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet known by the cultivar name Oregon and characterized by the combined features of large, non-dropping pink flowers with frilled edges, with a few flowers tending to semi-double; strong upright flower stems, and up to nine flowers per stem with the first flash of flowers, which occurs approximately eight weeks after potting.

1 Drawing Figure

The present invention comprises a new and distinct cultivar of African violet plant, botanically known as *Saintpaulia ionantha,* and hereinafter referred to by the cultivar name Oregon. The new cultivar, identified during the breeding and selection process by the designation b. 234/3-48/16, pink-frilled, is a product of a planned breeding program.

The new cultivar was originated from a cross made in a controlled breeding program in Isselburg, Rhineland, Germany. The female, or seed parent was T I pink frilled, an unpatented cultivar. The male, or pollen parent was XIX 4001 red, also unpatented, and was selected for breeding due to its upright flower stems and attractive leaves surrounding the flower bouquet.

The new cultivar Oregon was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Oregon, which in combination distinguish the African Violet as a new and distinct cultivar:

(1) Large non-dropping flowers having frilled edges.
(2) Pink flower color.
(3) A few flowers tend to semi-double.
(4) Strong upright flower stems.
(5) Up to 9 flowers per stem with first flash of flowers, which occurs approximately 8 weeks after potting.

The accompanying photographic drawing shows a typical specimen plant of the new cultivar. The colors appearing in the photograph are as true as possible with color illustrations of this type.

In the following description, color references are made to the Royal Horticultural Society (RHS) color chart, except where general color terms of ordinary significance are obvious.

Botanical classification: *Saintpaulia ionantha,* Ramat cv Oregon

Parentage:

*Male parent.*—XIX 4001 red.

*Female parent.*—FI pink frilled.

Propagation:

The new cultivar holds its distinguishing characteristics through successive propagations by leaf cuttings and by division of shoots.

Plant:

From 10 cm. to 12 cm. tall when grown in pots, and approximately 28 cm. in diameter when fully grown.

*Leaves.*—General form: oval. Diameter: 70 mm. Texture: soft, slightly hairy. Aspect: slightly shiny; velvety. Veins: well pronounced, light green. Color (upperside): 131 A. Color (underside): 64A. Petiole: brownish red.

Flowers:

*Buds.*—Ballshaped, 8 mm. in diameter, color 186D.

*Sepals.*—Five, spear-shaped. Color: 187A. Calyx: funnel-shaped. Aspect: spear-shaped. Peduncle: brown-red, slightly hairy.

Individual flowers:

*Size.*—Up to 50 mm. in total diameter.

*Color.*—Upperside: 68A-B. Underside: 68C.

*Borne.*—Up to 9 flowers per stem.

*Shape.*—2 small and 3 large petals, all of which are frilled at the edges. Corolla slightly cup-shaped.

*Arrangement.*—On very strong and upright flower stems.

*Flowering time.*—7–8 weeks after potting the first flowers appear, and a full flowerhead appears in two more weeks.

Reproductive organs:

*Stamens.*—Two, color 7B.

*Anthers.*—Four, color 7B.

*Arrangement.*—Two anthers, composed of two anther cells, which give the appearance of four anthers in each flower.

*Filaments.*—3–4 mm. long, round, green-yellow on pink-violet base.

*Styles.*—Color, light-pink on green base. Pollen color: 7-C.

Roots: white when young, brownish when older.

Disease resistance: good to date.

General observations:

Oregon is a vigorous pink frilled African violet. After 8 weeks the plant forms a nice flowerhead, and in 10 weeks the plant is in full flower. The flower stems are strong and upright, with up to 9 flowers per stem. The flowers remain, depending on temperature, 4–6 weeks.

I claim:

1. A new and distinct cultivar of African violet known by the cultivar name Oregon and characterized by the combined features of large, non-dropping pink flowers with frilled edges, with a few flowers tending to semi-double; strong upright flower stems, and up to nine flowers per stem with the first flash of flowers, which occurs approximately eight weeks after potting.

* * * * *

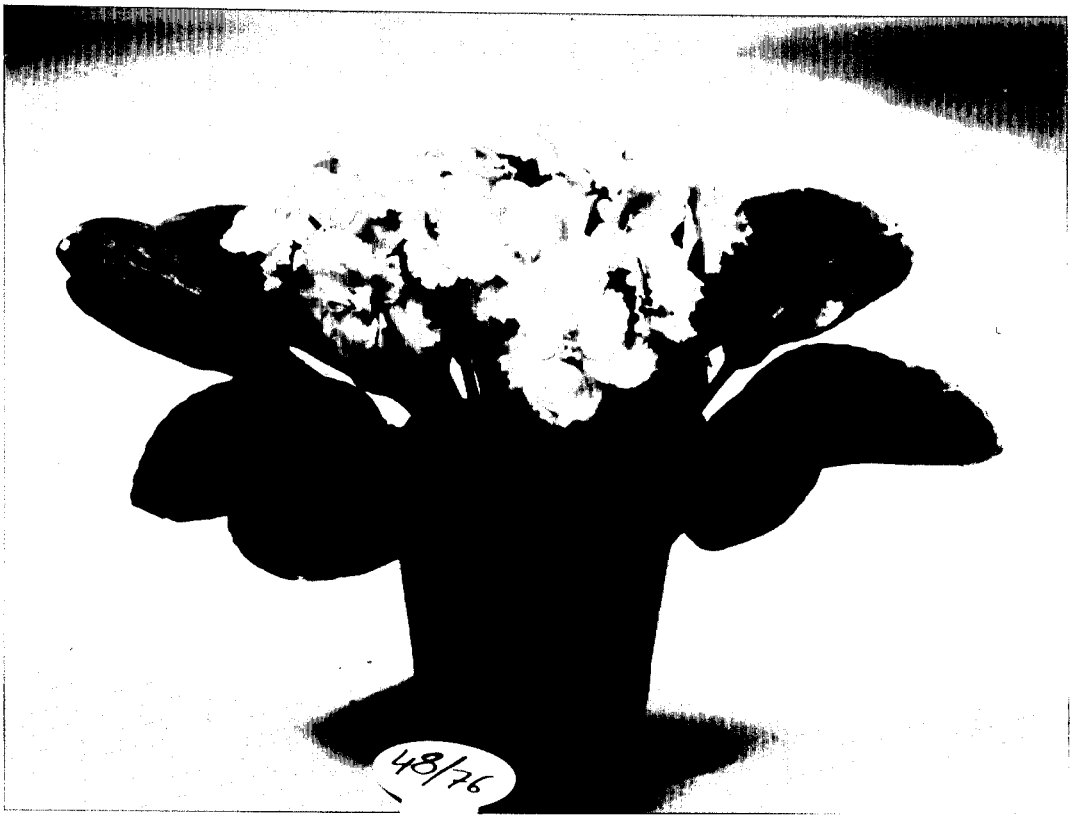
48/76